US011717566B2

(12) United States Patent
Arenas Gamboa et al.

(10) Patent No.: US 11,717,566 B2
(45) Date of Patent: Aug. 8, 2023

(54) *BRUCELLA CANIS* VACCINE FOR DOGS (71) Applicant: THE TEXAS A&M UNIVERSITY SYSTEM, College Station, TX (US)

(72) Inventors: Angela M. Arenas Gamboa, College Station, TX (US); Thomas A. Ficht, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 166 days.

(21) Appl. No.: 16/757,509

(22) PCT Filed: Oct. 19, 2018

(86) PCT No.: PCT/US2018/056703
§ 371 (c)(1),
(2) Date: Apr. 20, 2020

(87) PCT Pub. No.: WO2019/079716
PCT Pub. Date: Apr. 25, 2019

(65) Prior Publication Data
US 2020/0237891 A1    Jul. 30, 2020

Related U.S. Application Data

(60) Provisional application No. 62/575,144, filed on Oct. 20, 2017.

(51) Int. Cl.
*A61K 39/02* (2006.01)
*A61K 39/10* (2006.01)
*C12N 1/36* (2006.01)

(52) U.S. Cl.
CPC .............. *A61K 39/098* (2013.01); *C12N 1/36* (2013.01)

(58) Field of Classification Search
CPC ................................ C12N 1/36; A61K 39/098
See application file for complete search history.

(56) References Cited

U.S. PATENT DOCUMENTS

| 5,698,155 A | 12/1997 | Grosswald et al. |
| 7,541,447 B2 | 6/2009 | Ugalde et al. |
| 2005/0260258 A1 | 11/2005 | Ficht et al. |
| 2007/0036823 A1 | 2/2007 | Bandara et al. |
| 2011/0177127 A1 | 7/2011 | Andrews et al. |
| 2014/0248354 A1 | 9/2014 | Fight et al. |

FOREIGN PATENT DOCUMENTS

WO    20190079716 A1    4/2019

OTHER PUBLICATIONS

Allen, et al. "Transposon-derived *Brucella abortus* rough mutants are attenuated and exhibit reduced intracellular survival" Infection and immunity, 1998, 66:1008-1016.

Arenas-Gamboa, et al. "The *Brucella abortus* S19 DeltavjbR live vaccine candidate is safer than S19 and confers protection against wild-type challenge in BALB/c mice when delivered in a sustained-release vehicle" Infection and immunity, 2009, 77:877-884.

Bahlawane, et al. 2008. Sinorhizobium meliloti regulator MucR couples exopolysaccharide synthesis and motility. Mol Plant Microbe Interact 21:1498-1509.

Bossi, et al. Bichat guidelines for the clinical management of brucellosis and bioterrorism-related brucellosis. Euro Surveill, 2004, 9:E15-16.

Cassataro, et al. "A DNA vaccine coding for the *Brucella* outer membrane protein 31 confers protection against *B. melitensis* and B. ovis infection by eliciting a specific cytotoxic response". Infection and immunity, 2005, 73:6537-6546.

Cespedes, et al. "Identification and partial characterisation of a new protective antigen of *Brucella abortus*" Journal of medical microbiology, 2000, 49:165-170.

Costerton, et al. "Microbial biofilms" Annual review of microbiology, 1995, 49:711-745.

Ficht, et al. "Brucellosis: the case for live, attenuated vaccines" Vaccine 27, 2009 Suppl 4:D40-43.

Ficht, et al. "In vitro mutagenesis of *brucella* species" Methods in molecular biology, 2010 (Clifton, N.J 634:15-35.

Hay, et al. "MucR, a novel membrane-associated regulator of alginate biosynthesis in Pseudomonas aeruginosa" Applied and environmental microbiology, 2009, 75:1110-1120.

Hong, et al. "Identification of genes required for chronic persistence of *Brucella abortus* in mice" Infection and immunity, 2000, 68:4102-4107.

Kahl-McDonagh, et al. 2006. Evaluation of novel *Brucella melitensis* unmarked deletion mutants for safety and efficacy in the goat model of brucellosis. Vaccine 24:5169-5177.

Kahl-McDonagh, et al. "Aerosol infection of BALB/c mice with *Brucella melitensis* and *Brucella abortus* and protective efficacy against aerosol challenge" Infection and immunity, 2007, 75:4923-4932.

Montaraz, et al. "Comparison of living and nonliving vaccines for *Brucella abortus* in BALB/c mice" Infection and immunity, 1986, 53:245-251.

Onate, et al. "A DNA vaccine encoding Cu,Zn superoxide dismutase of *Brucella abortus* induces protective immunity in BALB/c mice" Infection and immunity, 2003, 71:4857-4861.

Pasquevich, et al. "Immunization with recombinant *brucella* species outer membrane protein Omp16 or Omp19 in adjuvant induces specific CD4+ and CD8+ T cells as well as systemic and oral protection against *Brucella abortus* infection" Infection and immunity, 2009, 77:436-445.

Spink, et al. "Immunization with viable *Brucella* organisms. Results of a safety test in humans" Bull World Health Organ, 1962, 26:409-419.

(Continued)

Primary Examiner — Satyendra K Singh
(74) Attorney, Agent, or Firm — Edwin S. Flores; Daniel J. Chalker; Chalker Flores, LLP (57) ABSTRACT

Methods and compositions for the treatment of *Brucella* induced diseases and disorders are disclosed herein. In preferred embodiments, the invention relates to a vaccine compositions and methods of vaccinating comprising: a *Brucella canis* comprising one or more attenuating gene knockouts; and a pharmaceutically acceptable vaccine carrier.

6 Claims, 3 Drawing Sheets

(56) References Cited

OTHER PUBLICATIONS

United States Patent and Trademark Office (ISA) International Search Report and Written Opinion for PCT/US2018/056703 dated Feb. 21, 2019, 10 pp.
Wu, et al. "Mariner mutagenesis of *Brucella melitensis* reveals genes with previously uncharacterized roles in virulence and survival" BMC Microbiol, 2006, 6:102.
Perkins, et al. "Towards a *Brucella* vaccine for humans" FEMS microbiology reviews, Final version published online Feb. 18, 2010.

PERCENT MAXIMUM CYTOTOXICITY OVER 48 HOURS

- ○ B. canis
- □ B. canisΔvjbR
- △ UNINFECTED CELLS

Y-axis: % MAXIMUM CYTOTOXICITY
X-axis: TIME POST-INFECTION (HOURS)

START

605 — IDENTIFYING THE HUMAN OR ANIMAL SUBJECT IN NEED OF THE PROPHYLAXIS, AMELIORATION OF SYMPTOMS, OR ANY COMBINATIONS THEREOF AGAINST BRUCELLOSIS; AND

615 — ADMINISTERING A THERAPEUTICALLY EFFECTIVE AMOUNT OF A VACCINE COMPOSITION TO THE HUMAN OR ANIMAL SUBJECT FOR THE PROPHYLAXIS, AMELIORATION OF SYMPTOMS, OR ANY COMBINATIONS THEREOF AGAINST BRUCELLOSIS, WHEREIN THE VACCINE COMPRISES:

620 — A BRUCELLA CANIS STRAIN COMPRISING ONE OR MORE ATTENUATING GENE KNOCKOUTS; AND

625 — AN OPTIONAL ADJUVANT OR A PHARMACEUTICALLY ACCEPTABLE CARRIER

STOP

BRUCELLA CANIS VACCINE FOR DOGS

CROSS-REFERENCE TO RELATED APPLICATIONS

This application is a National Stage of International Application No. PCT/US2018/056703, filed Oct. 19, 2018, which claims the benefit of U.S. Provisional Application No. 62/575,144, filed Oct. 20, 2017. The contents of each of which are incorporated by reference in their entirety.

TECHNICAL FIELD OF THE INVENTION

The present invention relates in general to methods and compositions for the treatment of *Brucella* induced diseases and disorders in dogs and humans.

STATEMENT OF FEDERALLY FUNDED RESEARCH

Not applicable.

REFERENCE TO A SEQUENCE LISTING

Not applicable.

BACKGROUND OF THE INVENTION

Without limiting the scope of the invention, its background is described in connection with controlled release vaccines and use of *Brucella* strains in vaccine manufacturing.

Andrews and Lowry have described compositions and methods for the diagnosis and prevention of *B. abortus* infection in U.S. Patent Application Publication No. 2011/0177127. The invention describes a method of detecting a *Brucella abortus* infection in an animal, comprising the steps of: a) obtaining a biological sample from said animal; and b) detecting the presence of at least one antibody immunologically specific for at least one *Brucella abortus* protein, wherein the presence of antibodies to the *Brucella abortus* protein indicates a *Brucella abortus* infection in said animal.

At present, no human brucellosis vaccine is available even though *Brucella* species are isolated from 86 countries, with 500,000 new cases of brucellosis appearing each year throughout Latin America, the Mediterranean littoral, Arabian peninsula, Africa, central Asia and the Far East (WHO, 2006); as a result, prevention of human brucellosis has focused upon the reduction in animal disease. The animal vaccine strains employed today are fortuitous isolates attenuated in ability to cause abortion due to reduced replication in reproductive tissues. The attenuation of these mutants does not extend to reticuloendothelial disease observed in mice and in humans, except in the case of the rough strain RB51. The lack of genetic definition of fortuitous isolates limits the usefulness of vaccine strains, preventing complete description of their stability, and warrants caution when applied to human use as disclosed in Sangari et al (1998) *Vaccine* 16, 1640-5 and Schurig et al (1991) *Vet. Microbiol.* 28, 171-88. Of the currently available vaccine strains, only *B. abortus* S19 and *B. melitensis* Rev1 have been tested in humans as provided for in Spink et al. *Bull World Health Organ* (1962) 26, 409-19 and Spink & Thompson (1953) *JAMA* 153, 1162-1165, which are hereby incorporated by reference. Rev1 was found to be highly unsuitable with ⅔ of the "volunteers" exhibiting symptoms of disease and colonization by the organism. However, a subculture of S19 referred to as 19-BA provided results that are more palatable. Only two volunteers (12%) exhibited symptoms of disease, and the organism was isolated from one of these volunteers. 19-BA was originally used to vaccinate at least 3 million people in the Soviet Union as described in Vershilova Bull World Health Organ (1961) 24, 85-9. These investigators concluded that there were more problems due to hypersensitivity than to persistence of the organism. Eight percent complained of headache and malaise, and 2% showed signs of febrile illness. Clearly, a vaccine with this much side effect would not be and should not be tolerated given our current state of knowledge. Given the potential threat this organism poses, there is a need to develop a better human vaccine.

One such example of a live vaccine against brucellosis is described in U.S. Pat. No. 7,541,447 issued to Ugalde et al. (2009). The Ugalde invention comprises a live vaccine for immunization, prophylaxis or treatment of brucellosis comprising a bacterium modified by partial or complete deletion of the pgm gene, rendering the bacterium incapable of synthesizing a key enzyme in the metabolism of bacterial sugars. The vaccine of the '447 patent discloses nucleotide sequence fragments having the aforementioned deletion and is either lyophilized or is in a pharmaceutical vehicle.

SUMMARY OF THE INVENTION

The present invention relates to methods and compositions for the treatment of *Brucella* induced diseases and disorders. In preferred embodiments, the invention relates to vaccines.

In one embodiment, the present invention includes a vaccine composition comprising: a *Brucella canis* comprising one or more attenuating gene knockouts; and a pharmaceutically acceptable vaccine carrier. In one aspect, the composition comprises an optional adjuvant. In another aspect, the attenuating gene knockout is selected from the group consisting of ΔvjbR and 16M ΔvjbR. In another aspect, the vaccine composition further comprises a diagnostic gene knockout comprises a differentiation of infected animals from vaccinated animals (DIVA) mutant that includes ΔvirB12, Δbcsp31, Δasp24, or proteins in Table 1. In another aspect, the attenuating gene knockout further comprises deletions of ΔmucR, ΔvirB2, or ΔmanB/A. In another aspect, the vaccine comprises ΔvjbR/DIVA, 16MΔvjbR/DIVA, or any combinations thereof. In another aspect, the vaccine composition further comprises expressing one or more optional antibiotic resistance genes in the *Brucella canis*. In another aspect, the vaccine is used for a prophylaxis, an amelioration of symptoms, a treatment, or any combinations thereof against brucellosis in a human or an animal subject. In another aspect, the vaccine is administered by an oral, an intranasal, a parenteral, an intradermal, an intramuscular, an intraperitoneal, an intravenous, a subcutaneous, an epidural, a mucosal, a rectal, a vaginal, a sublingual, or a buccal route. In another aspect, the vaccine composition further comprises an encapsulating agent that is an alginate bead or a microsphere.

In another embodiment, the present invention includes a vaccine composition comprising: a *Brucella canis* comprising one or more attenuating gene knockouts selected from at least one of ΔvjbR and 16M ΔvjbR; and a pharmaceutically acceptable vaccine carrier. In one aspect, the composition comprises an adjuvant. In another aspect, the vaccine composition further comprises expressing one or more optional antibiotic resistance genes in the *Brucella canis*. In another aspect, the vaccine is used for a prophylaxis, an amelioration of symptoms, a treatment, or any combinations thereof against brucellosis in a human or an animal subject. In another aspect, the vaccine is administered by an oral, an intranasal, a parenteral, an intradermal, an intramuscular, an intraperitoneal, an intravenous, a subcutaneous, an epidural, a mucosal, a rectal, a vaginal, a sublingual, or a buccal route.

In another embodiment, the present invention includes a method for prophylaxis, amelioration of symptoms, or any combinations thereof against brucellosis in a human or animal subject comprising the steps of: identifying the human or animal subject in need of the prophylaxis, amelioration of symptoms, or any combinations thereof against brucellosis; and administering a therapeutically effective amount of a vaccine composition to the human or animal subject for the prophylaxis, amelioration of symptoms, or any combinations thereof against brucellosis, wherein the vaccine comprises: a *Brucella canis* strain comprising one or more attenuating gene knockouts; and a pharmaceutically acceptable carrier. In one aspect, the composition further comprises an adjuvant. In another aspect, the attenuating gene knockout is selected from the group consisting of ΔvjbR and 16M ΔvjbR. In another aspect, the *Brucella canis* further comprises a diagnostic gene knockout comprises a differentiation of infected animals from vaccinated animals (DIVA) mutant that includes ΔvirB12, Δbcsp31, Δasp24, or proteins in Table 1. In another aspect, the attenuating gene knockout further comprises deletions of ΔmucR, ΔvirB2, or ΔmanB/A. In another aspect, the vaccine comprises ΔvjbR/DIVA, 16MΔvjbR/DIVA, or any combinations thereof. In another aspect, the *Brucella canis* is a double mutant and further comprises a third mutation, wherein the third mutation is a marker for serological testing. In another aspect, the *Brucella canis* further comprises one or more antibiotic markers, and in one non-limiting example the antibiotic marker is Kanamycin. In another aspect, the vaccine is administered by an oral, an intranasal, a parenteral, an intradermal, an intramuscular, an intraperitoneal, an intravenous, a subcutaneous, an epidural, a mucosal, a rectal, a vaginal, a sublingual, or a buccal route. In another aspect, the method further comprises encapsulating the *Brucella canis* with an encapsulating agent that is an alginate bead or a microsphere.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an," and "the" are not intended to refer to only a singular entity, but include the general class of which a specific example may be used for illustration. The terminology herein is used to describe specific embodiments of the invention, but their usage does not delimit the invention, except as outlined in the claims.

As used herein, "*Brucella*" refers to a genus of Gram-negative bacteria. They are small, non-motile, encapsulated coccobacilli. While not limiting the scope of the present invention, *Brucella* is often transmitted by ingesting infected food, direct contact with an infected animal, or inhalation of aerosols.

As used herein, "splenomegaly" refers to a disease characterized by an enlargement of the spleen. While not limiting the scope of the present invention, symptoms of splenomegaly include but are in no way limited to abdominal pain, early satiety due to splenic encroachment or anemia related symptoms.

As used herein, the term "brucellosis" refers to a disease caused by ingestion of milk or meat and/or contact with the bodily fluids or secretions of animals infected with *Brucella* bacterial species. While not limiting the scope of the present invention, symptoms of brucellosis include but are not limited to acute undulating fever, headache, night sweats, fatigue, sterility and anorexia.

As used herein, the terms "prevent" and "preventing" include the prevention of the recurrence, spread or onset of a disease or disorder. It is not intended that the present invention be limited to complete prevention. In some embodiments, the onset is delayed, or the severity of the disease or disorder is reduced.

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

The term "subject" as used herein refers to any mammal, preferably a human patient, livestock, or domestic pet. It is intended that the term "subject" encompass both human and non-human mammals, including, but not limited to canines, bovines, caprines, ovines, equines, porcines, felines, canines, etc., as well as humans. In preferred embodiments, the "subject" is a canine (e.g., a dog) or a human and it is not intended that the present invention be limited to these groups of animals.

As used herein the term "immunogenically-effective amount" refers to that amount of an immunogen required to generate an immune response (e.g. invoke a cellular response and/or the production of protective levels of antibodies in a host upon vaccination).

In a specific embodiment, the term "pharmaceutically acceptable" means approved by a regulatory agency of the federal or a state government or listed in the U.S. Pharmacopeia or other generally recognized pharmacopeia for use in animals, and more particularly in humans.

The term "carrier" as used herein refers to a diluent, adjuvant, excipient or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a subject, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The present compositions, if desired, can also contain minor amounts of wetting or emulsifying agents, or pH buffering agents.

The present invention relates to methods and compositions for the treatment of *Brucella* induced diseases and disorders. In preferred embodiments, the invention relates to vaccines. In additional embodiments, the invention relates to formulations capable of releasing said live vaccines at a controlled rate of release in vivo. In further embodiments, the invention relates to modified strains of the bacteria *Brucella canis*. In still further embodiments, the invention relates to compositions that do not induce splenomegaly in a subject receiving said compositions.

In preferred embodiments, the present invention relates to the treatment and prevention of *Brucellosis* induced diseases and disorders. To date, *Brucella* species have been isolated from humans and domesticated animals in nearly 90 countries, with an estimated 500,000 new cases each year. Moreover, *Brucella* species exhibit desirable characteristics for use as bioterrorism agents as described in Kaufmann et al. (1997) *Emerging Infectious Diseases* 3, 83-94 and Pappas et al. *Cell Mol Life Sci* (2006) 63, 2229-36, incorporated herein by reference. Thus, vaccines exhibiting prolonged interaction with the immune system combined with the safety of attenuated *Brucella* strains deliverable vaccines would be desirable.

A further embodiment of the present invention involves the use of double knockout, live *B. canis* mutants that are delivered orally, e.g., alone or using microencapsulation-mediated controlled release compositions. These compositions are storage-stable and compatible with a number of pharmaceutical agents. At this time and following decades of testing, the only effective vaccines for the prevention of brucellosis are living *Brucella* cells that stimulate the immune system through limited infection. Alternatives to the use of live, attenuated *Brucella* vaccines, including subunit vaccines and killed *Brucella*, have thus far proven non-efficacious. Live *Brucella* vaccines have been applied for decades to prevent brucellosis in cattle and sheep, but their capacity for direct use in humans has remained elusive. Previous reports have postulated that use of attenuated strains appropriate for use in humans is difficult, since spontaneously derived strains retain some level of virulence and are genetically undefined as disclosed in Spink et al. (1962) *Bulletin of the WHO* 26, 409-19, incorporated herein by reference. Recent evaluation of attenuated mutants has confirmed the superiority of long-term survival in stimulating a protective immune response, yet the added safety of short-term survival cannot be overlooked in the development of human vaccines. The present invention combines the optimal features of prolonged interaction with the immune system with enhanced safety of highly attenuated, single and/or double gene deletion *Brucella* mutants as a composition that is safe, free of side effects and efficacious in humans.

*Brucella* organisms can be delivered via aerosol to infect humans. The use of *Brucella* as a weapon was calculated to pose a substantial financial risk as disclosed in Kaufmann et al. (1997) *Emerging Infectious Diseases* 3, 83-94 and Pappas et al. *Cell Mol Life Sci* (2006) 63, 2229-36, both incorporated herein by reference. Infection incapacitates human hosts with mostly flu-like symptoms, but will result in death if left untreated as provided for in Young E J (1995) *Clin Inf Dis* 21, 283-290, hereby incorporated by reference. Bioengineering poses the additional risk of introducing antibiotic resistance, rendering ineffective the most successful form of treatment. The transposon Tn10 encoding tetracycline resistance has been used to obtain stable transformants. The financial impact study did not attempt to determine the threshold at which financial risk may pose a risk to national security. Nor did the study outline scenarios in which the use of one organism might be favored over the use of others. The study did underscore the need to invest in research in all understudied organisms to prevent their use in this manner and suggested that decreased study of these organisms increase the potential consequences resulting from their use as weapons. *Brucella* spp. have been weaponized by several countries, including the former Soviet Union, Japan and the USA, and thus is a recognized biological warfare threat that can cause illness and death in humans. No vaccine for humans is available against this threat. Expected market and commercial need: The primary need for human brucellosis vaccines is for specialty protection of military personnel, public health workers and veterinarians with the cross-over opportunity for extensive markets in the high risk zones that occur throughout the world, particularly in the Middle East, Central Asia, Latin-America, Africa and the Far East. While there is a huge need for a human brucellosis vaccine world-wide, the question is whether or not major biologics manufacturers will recognize these needs as a profitable market, thus it is more plausible that federal government subsidized stockpiles, e.g., Bioshield I and Bioshield II, to protect the general public and military personnel represent a more likely market. The potential reluctance of the general population to use live vaccines is based on a limited trust of scientists and government, and such thinking must not be used to deter the development of products based on otherwise sound scientific principles. The use of such vaccines in humans is expected under extreme circumstances, such as stockpiling large reserves for protection against biological terrorism or biological warfare. Starting with the work of Louis Pasteur, live vaccines have offered the best possible solution for immune protection. Use in humans requires that safety be determined beyond a shadow of a doubt. Questions concerning the preliminary production under Good Manufacturing Procedures and safety testing of such products warrant studies in non-human primate models.

As previously mentioned, no federally approved or commercially available human brucellosis vaccines are available anywhere worldwide; there simply are no currently known or published existing vaccine alternatives to protect humans from *Brucella canis*.

The present invention provides for controlled release compositions further comprising attenuated, live *Brucella canis* mutant vaccines. Drug delivery materials have historically been derived from many sources including commodity plastics and textile industries and have been incorporated into vehicles as diverse as pH responsive hydrogels and polymer microparticles or implants designed for surface or bulk erosion as disclosed in Langer RaP, N. A. (2003) *Bioengineering, Food and Natural Products* 49, 2990-3006, incorporated herein by reference. In the case of controlled release formulations, a drug is typically released by diffusion, erosion or solvent activation and transport. In most cases, the desired polymer characteristics include biocompatibility, lack of immunogenicity, capability of breakdown by the body and water solubility. Many of the processes used to entrap pharmaceuticals involve harsh organic solvents which are bacteriocidal and capable of denaturing proteins. When considering controlled release vehicles for the entrapment of active enzymes or living cells, new alternatives are needed. A number of milder processes based on established technologies and variations have recently been applied to the delivery of active protein agents such as insulin, erythropoietins and chemokines as provided for in Marschutz et al (2000) *Biomaterials* 21, 1499-07. Takenaga et al (2002) *J Control Release* 79, 81-91. and Qiu et al (2003) *Biomaterials* 24, 11-18., all of which are incorporated by reference, or as encapsulants for living cells to permit transplantation as disclosed in Young et al (2002) *Biomaterials* 23, 3495-3501, hereby incorporated by reference. The technologies cover a wide range of materials including gelatin-based hydrogels, protein-PEG microparticles, novel PEG copolymers, biodegradable PLGA particles, PLG/PVA microspheres and surface modified nanospheres. Alginate, a naturally occurring biopolymer, is especially well suited to the entrapment of living cells. Alginate is a linear unbranched polysaccharide composed of 1-4'-linked β-D-mannuronic acid and α-L-guluronic acids in varying quantities. Alginate polymers are highly water-soluble and easily crosslinked using divalent cations such as Ca2+ or polycations such as poly-L-lysine as provided for in Wee & Gombotz (1998) *Adv Drug Deliv Rev* 31, 267-285, hereby incorporated by reference. The relatively mild conditions required to produce either an alginate matrix or particle is compatible with cell viability. Entrapment in alginate has been shown to greatly enhance viability and storage as provided for in Cui et al (2000) *Int J Pharm* 210, 51-59 and Kwok et al (1989) *Proc. Int. Symp. Contol. Release Bioact. Mater.* 16, 170-171, both of which are incorporated by reference. The physical properties such as porosity, rate of erosion, and release properties may be modulated through mixing alginates of different guluronic acid composition and through applying different coatings to the matrix as provided for in Wee & Gombotz (1998) Adv Drug Deliv Rev 31, 267-285. While in no way limiting the scope of the present invention, it is generally thought that release of a biomolecule from alginate matrices generally occurs through i) diffusion through pores of the polymer or ii) erosion of the polymer network. In general, the alginate matrix is stabilized under acidic conditions, but erodes slowly at pH of 6.8 or above.

The present invention exploits the performance and safety of live *Brucella* strains, which have been rendered safe by the elimination of certain genes that attenuate the *Brucella*, and in this particular case, *Brucella canis*.

It is also possible to stabilize the attenuated bacteria (or spores thereof) in a slow erosion capsule, resulting in a prolonged release of bacteria. A further advantage of the present invention is that highly attenuated, safe, and may also include a double, triple or more gene deletion(s), live *Brucella canis* mutants can be safely delivered orally by controlled release to optimally provide the long term immunostimulation required for protective immunity. As previously mentioned, currently available *Brucella canis* vaccines are unsuitable for human use, and antibiotic therapies are at best unreliable and ineffective, particularly if, e.g., bioterrorists introduce antibiotic resistance into weaponized strains of *B. canis*. Vaccination offers the best approach for long-range protection. In view of the lack of success of defining *Brucella* protective immunogens over the last four decades, the use of attenuated vaccine strains offers the best approach. Data reported below includes the identification of genetic defects that specifically attenuate intracellular survival. These strains have been characterized based on safety and attenuation in the mouse and goats and soon in non-human primates. The most protective strains are less attenuated, survive longer in the host and cause unwanted side effects (e.g., splenomegaly). The aim of the proposed studies is to utilize the most attenuated mutants and enhance vaccine potential through sustained release ultimately in non-human primates, to list a very specific and defined product.

There is strong support for oral vaccination with alginate and alginate/protein encapsulated strains as disclosed in Arenas-Gamboa et al. *Infect Immun* (2008) vol. 76, 2448-55, Kahl-McDonagh et al (2007) *Infect Immun* 75, 4923-32, Suckow et al (2002) *J Control Release* 85, 227-235, Kim et al (2002) J *Control Release* 85, 191-202., all of which are hereby incorporated by reference. In addition, lyophilization of bacteria in alginate beads extends their viability. Embodiments of the present invention include a storage-stable delivery system that may be administered orally and is generally applicable to a number of select agents.

Pharmaceutical Formulations: The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). In one embodiment, the vaccine is encapsulated using materials described in U.S. Patent Application Publication No. 2005/0260258, hereby incorporated by reference.

In a preferred embodiment, the active compound and optionally another therapeutic or prophylactic agent are formulated in accordance with routine procedures as pharmaceutical compositions adapted for administration to human beings. Typically, the active compounds for administration are solutions in sterile isotonic aqueous buffer. Where necessary, the compositions can also include a solubilizing agent. Compositions for administration can optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the active compound is to be administered by infusion, it can be dispensed, for example, with an infusion bottle containing sterile pharmaceutical grade water or saline. Where the active compound is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for an oral administration of the active compound. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, and the like. Such vehicles are preferably of pharmaceutical grade.

Further, the effect of the active compound can be delayed or prolonged by proper formulation. For example, a slowly soluble pellet of the active compound can be prepared and incorporated in a tablet or capsule. The technique can be improved by making pellets of several different dissolution rates and filling capsules with a mixture of the pellets. Tablets or capsules can be coated with a film that resists dissolution for a predictable period of time. Even the parenteral preparations can be made long acting, by dissolving or suspending the compound in oily or emulsified vehicles, which allow it to disperse only slowly in the serum.

Compositions for use in accordance with the present invention can be formulated in conventional manner using one or more physiologically acceptable carriers or excipients.

Thus, the compound and optionally another therapeutic or prophylactic agent and their physiologically acceptable salts and solvates can be formulated into pharmaceutical compositions for administration by inhalation or insufflation (either through the mouth or the nose) or oral, parenteral or mucosal (such as buccal, vaginal, rectal, sublingual) administration. In some embodiments, the administration is ophthalmic (e.g. eyes drops applied directly to the eye). In one embodiment, local or systemic parenteral administration is used.

For oral administration, the compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound. The microencapsulated vaccine gives a controlled release or continual boosting effect. Those formulations with vpB and alginate are described in U.S. Patent Application Publication No. 2005/0260258, hereby incorporated by reference.

For buccal administration the compositions can take the form of tablets or lozenges formulated in conventional manner.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compositions can be formulated for parenteral administration by injection, e.g., by bolus injection or continuous infusion. Formulations for injection can be presented in unit dosage form, e.g., in ampoules or in multi-dose containers, with an added preservative. The pharmaceutical compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

In addition to the formulations described previously, the compositions can also be formulated as a depot preparation. Such long acting formulations can be administered by implantation (for example subcutaneously or intramuscularly) or by intramuscular injection. Thus, for example, the pharmaceutical compositions can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

In certain preferred embodiments, the pack or dispenser contains one or more unit dosage forms containing no more than the recommended dosage formulation as determined in the Physician's Desk Reference ($62^{nd}$ ed. 2008, herein incorporated by reference in its entirety).

Methods of administering the active compound and optionally another therapeutic or prophylactic agent include, but are not limited to, parenteral administration (e.g., intradermal, intramuscular, intraperitoneal, intravenous and subcutaneous), epidural, and mucosal (e.g., intranasal, rectal, vaginal, sublingual, buccal or oral routes). In a specific embodiment, the active compound and optionally other prophylactic or therapeutic agents are administered intramuscularly, intravenously, or subcutaneously. The active compound and optionally other prophylactic or therapeutic agents can also be administered by infusion or bolus injection and can be administered together with other biologically active agents. Administration can be local or systemic. The active compound and optionally the prophylactic or therapeutic agent and their physiologically acceptable salts and solvates can also be administered by inhalation or insufflation (either through the mouth or the nose). In a preferred embodiment, local or systemic parenteral administration is used.

Pulmonary administration can also be employed, e.g., by use of an inhaler or nebulizer, and formulation with an aerosolizing agent, or via perfusion in a fluorocarbon or synthetic pulmonary surfactant. In certain embodiments, the active compound can be formulated as a suppository, with traditional binders and vehicles such as triglycerides.

Selection of a particular effective dose can be determined (e.g., via clinical trials) by a skilled artisan based upon the consideration of several factors, which will be known to one skilled in the art. Such factors include the disease to be treated or prevented, the symptoms involved, the subject's body mass, the subject's immune status and other factors known by the skilled artisan.

The dose of the active compound to be administered to a subject, such as a human, is rather widely variable and can be subject to independent judgment. It is often practical to administer the daily dose at various hours of the day. However, in any given case, the amount administered will depend on such factors as the viability of the active component, the formulation used, subject condition (such as weight), and/or the route of administration.

Canine brucellosis is a contagious disease caused by *Brucella canis*. *B. Canis* primarily affects the reproductive system of dogs, causing mid-late term abortions, infertility, and orchitis. Transmitted by contact with infected body fluids or tissues, in particular during breeding or birth. *B. Canis* is a zoonotic pathogen and human/canine infections are on the rise due to chronic persistence of the organism, low infectious dose, and low sensitivity and specificity of current diagnostic tests. Brucellosis may cause systemic infection in dogs and humans, leading to complications such as endocarditis and diskospondylitis. The vjbr gene encodes the luxr-like quorum sensing-related transcriptional regulator required for the virb type IV secretion system expression→required for virulence in mice and survival in macrophages. No vaccine approved for use in dogs against *Brucella* spp and no effective treatment.

The aim of this study was to evaluate a live attenuated vaccine for canine brucellosis by the deletion of the vjbR gene (bab2_0118) and to assess the attenuation and immune potential of the vaccine strain in vitro.

Canine macrophage-like cells (DH82, ATCC CRL-10389) were cultured in eagle's minimum essential media-EMEM (containing 1-glutamine) with 15% fetal bovine serum. Monolayers of macrophages containing $2.5 \times 10^5$ cells were infected with *Brucella canis*, *B. canis* δvjbr, *B. suis*, *B. abortus* s19, s19 δvjbr, *B. melitensis* (16 m), and 16 m δvjbr, at a multiplicity of infection (MOI) of 1:100, centrifuged at 1000 rpm for 5 minutes, and incubated at 37° C. and 5% $CO_2$ for 30 minutes. Macrophages were then washed twice with fresh media and incubated at 37° C. with gentamicin to kill any extracellular bacteria. Cells were lysed with 0.5% tween 20 in distilled water and serial dilutions were plated onto TSA at 1, 24, and 48-hours post infection. Culture supernatants were collected at each time point prior to lysis and lactate dehydrogenase (LDH) levels were measured using the Promega cytotox 96 non-radioactive cytotoxicity assay, and compared to maximum LDH release. Colonies were counted 3 days after plating to assess entry, survival, and replication within the cells.

Figure 1:
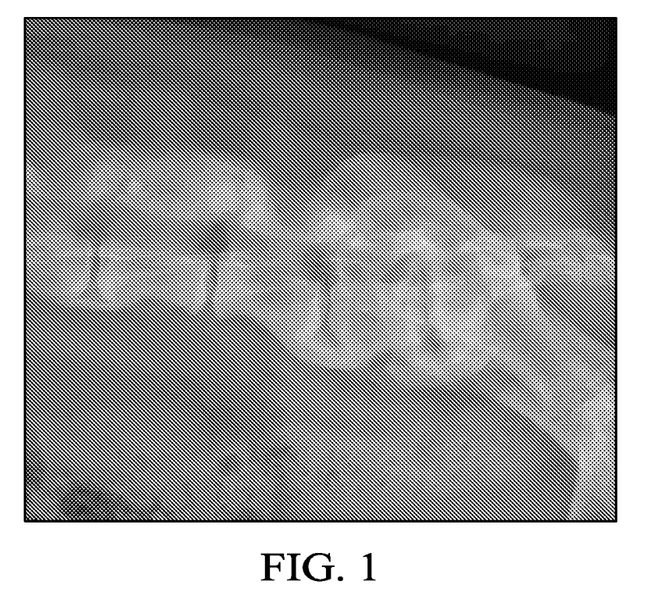
FIG. 1 shows diskospondylitis in a dog with brucellosis.
Figure 2:
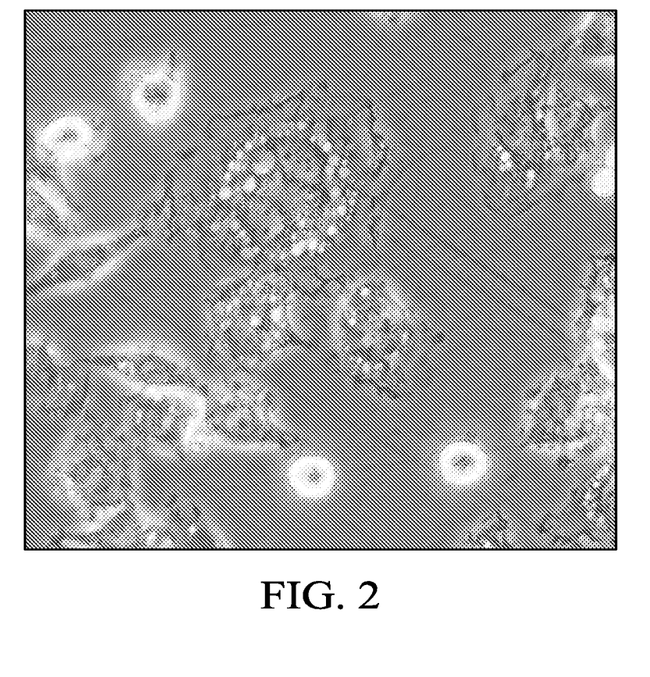
FIG. 2 shows Canine DH82 macrophage-like cells.

FIG. 1 shows diskospondylitis in a dog with brucellosis. FIG. 2 shows Canine DH82 macrophage-like cells.

*Brucella canis* successfully entered inside cells at a level similar to that observed for other *Brucella* strains. By 24 and 48 hours post-infection, bacterial numbers for *B. canis, B. canis* ΔvjbR, 16M ΔvjbR, and S19 ΔvjbR significantly and progressively decreased. Bacterial numbers for *B. suis* and S19 decreased after 24 hours post-infection but significantly increased by 48 hours post-infection while 16M increased after 24 hours but significantly decreased by 48 hours post-infection. The numbers of *B. canis* and *B. canis* ΔvjbR were not significantly different at 24 hours post-infection but numbers of *B. canis* ΔvjbR were significantly lower than *B. canis* at 48 hours post infection. The numbers of S19 and 16M were significantly higher at 48 hours post infection compared to the mutants S19 ΔvjbR and 16M ΔvjbR, respectively. LDH release was not significantly different between *B. canis, B. canis* ΔvjbR, and uninfected cells at any time point.

Figure 3:
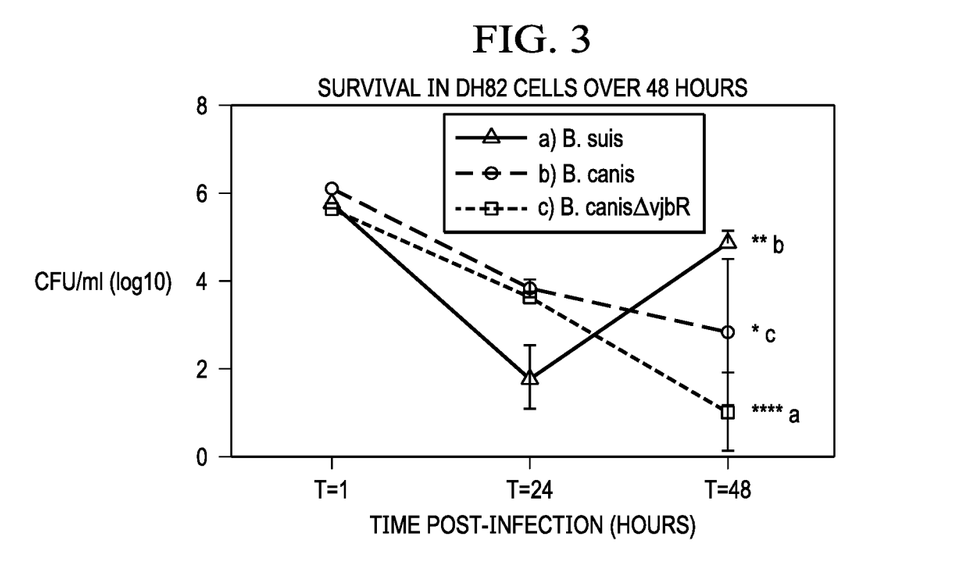
FIGS. 3 and 4 are graphs that show the number of colony forming units (CFU) of *Brucella* spp. per mL following infection of canine macrophage-like cells (DH82) after 1, 24 and 48 hours. Significant differences among groups are indicated as follows: *P<0.05, P<0.01, *P>0.001, ****P<0.0001.
Figure 4:
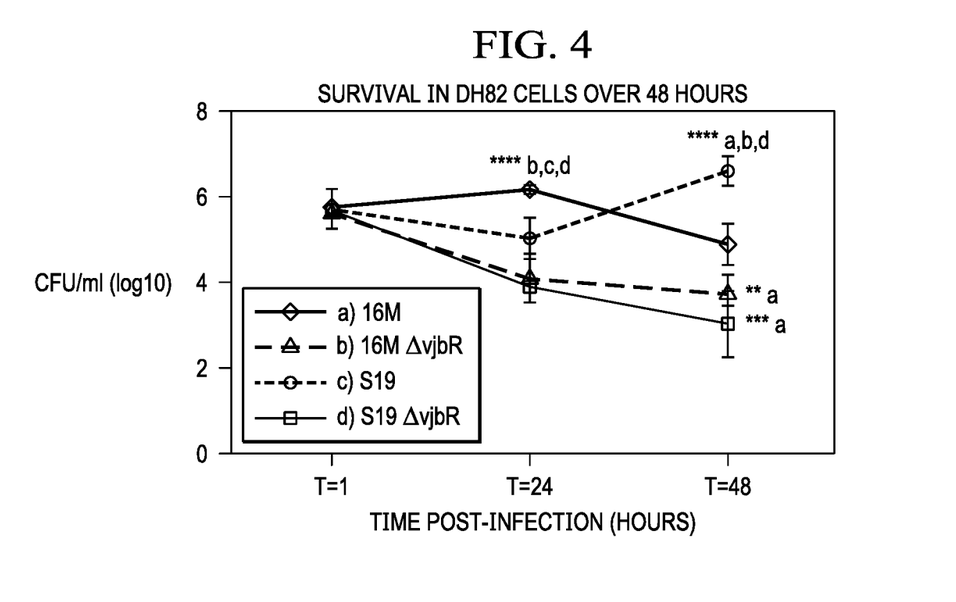

FIGS. 3 and 4 are graphs that show the number of colony forming units (CFU) of *Brucella* spp. per mL following infection of canine macrophage-like cells (DH82) after 1, 24 and 48 hours. Significant differences among groups are indicated as follows: *$P<0.05$, $P<0.01$, *$P>0.001$, ****$P<0.0001$.

Figure 5:
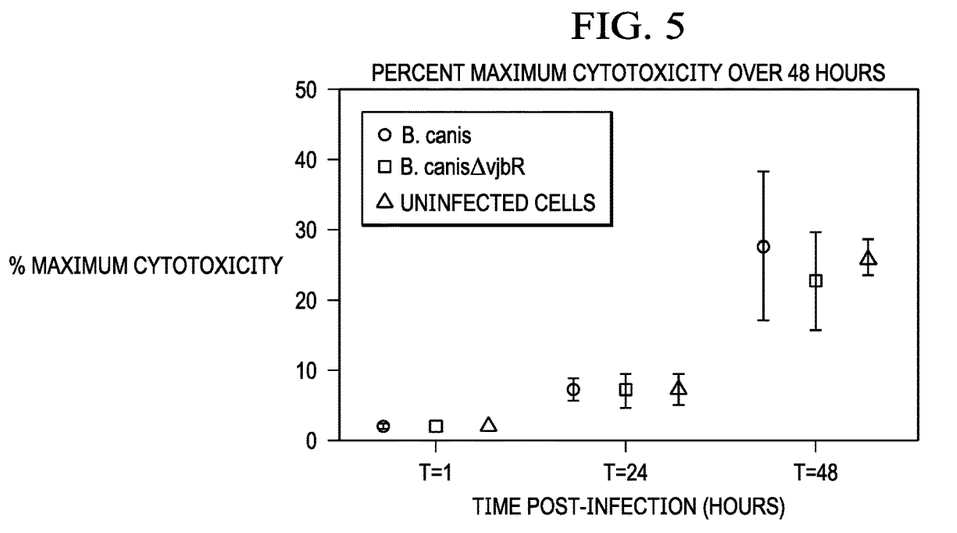
FIG. 5 is a graph that shows the percentage of maximum lactate dehydrogenase (LDH) release following infection of canine macrophage-like cells (DH82) after 1, 24 and 48 hours.

FIG. 5 is a graph that shows the percentage of maximum lactate dehydrogenase (LDH) release following infection of canine macrophage-like cells (DH82) after 1, 24 and 48 hours.

Figure 6:
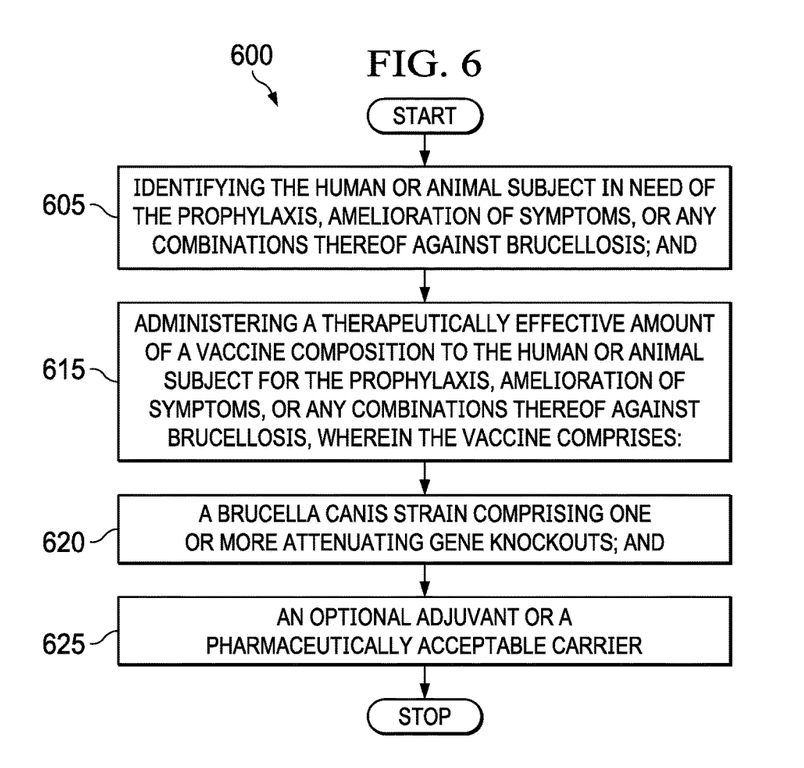
FIG. 6 is a flow chart of a method of the present invention.

FIG. 6 is a flow chart 600 of the method of the present invention. In the first step, 605, a human or animal subject in need of the prophylaxis, amelioration of symptoms, or any combinations thereof against brucellosis. Next, in step 615, a therapeutically effective amount of a vaccine composition to the human or animal subject for the prophylaxis, amelioration of symptoms, or any combinations thereof against brucellosis, wherein the vaccine comprises, a *Brucella canis* strain comprising one or more attenuating gene knockouts (step 620); and an optional adjuvant or a pharmaceutically acceptable carrier (Step 625).

*Brucella canis, B. canis* ΔvjbR, *B. suis*, and other *Brucella* strains enter macrophages at a comparable rate within 1 hour of infection. *B. suis*, which is pathogenic in dogs, as well as *B. abortus* S19 which is not pathogenic in dogs, demonstrate intracellular replication within DH82 cells at 48 hours. *B. canis* and *B. canis* ΔvjbR persist within DH82 cells to 48 hours post-infection but do not exhibit intracellular replication and are progressively killed by the macrophage-like cells. *B. canis* ΔvjbR is attenuated compared to *B. canis*, demonstrated by increased ability of DH82 cells to kill the mutant compared to the parental strain. The vjbR gene is important for *B. canis* virulence as it is in *B. abortus* S19 (cattle) and *B. melitensis* (sheep, goats). Moreover, *B. canis* is similar to smooth strains of *Brucella*, is not cytotoxic. Table 1 includes additional examples of proteins that may be used as DIVA markers, such that one or more of these proteins may be regulated by the mutants taught herein, e.g., proteins such as DegP and others are regulated by vjbR.

TABLE 1

Additional examples of proteins that may be used as DIVA markers.

| Immunodominant proteins observed in serum samples from infected animals and humans | B. canis product name/B. canis protein ID | Presence or absence in B. canis |
|---|---|---|
| OMP 10 (BME_RS10275/ BCAN_B0080) | Outer membrane lipoprotein Omp10 Protein ID = ABX63282.1 | + |
| OMP 16 (BME_RS01650/ BCAN_A1734) | Peptidoglycan-associated lipoprotein ProteinID = ABX62740.1 | + |
| GroEL (BME_RS15285/ BCAN_B0195) | Chaperonin GroEL Protein ID = ABX63389.1 | + |
| Antigen bp26/SIMPL domain-containing protein (BME_RS02675/BCAN_A1512) | 26 kDa periplasmic immunogenic protein precursor Protein ID = ABX62538.1 | + |
| Hypothetical Protein (BME_RS04020/BCAN_A1202) | Protein of unknown function DUF883 ElaB Protein ID = ABX62251.1 | + |
| DegP-like serine endoprotease (BME_RS06695/ BCAN_A0627) | Protease Do Protein ID = ABX61702.1 | + |
| Transporter (BME_RS09370/ BCAN_A0055) | Protein of unknown function DUF461 Protein ID = ABX61159.1 | + |
| HTH-type quorum sensing-dependent transcriptional regulator VjbR(BME_RS15625/ BCAN_B0123) | Regulatory protein LuxR Protein ID = ABX633 21.1 | + |
| ABC transporter substrate-binding protein (BME_RS13590/ BCAN_B0576) | Extracellular solute-binding protein family 5" Protein ID = ABX63753.1 | + |
| Type IV secretion system protein virB5 (BME_RS10335/ BCAN_B0068) | P-type DNA transfer protein VirB5 Protein ID = ABX63270.1 | + |

Thus, using the present invention it is possible to isolate and culture normal canine macrophages from bone marrow for further in vitro testing and investigation of the immune potential of B. canis ΔvjbR in vivo beginning with a mouse model.

It is contemplated that any embodiment discussed in this specification can be implemented with respect to any method, kit, reagent, or composition of the invention, and vice versa. Furthermore, compositions of the invention can be used to achieve methods of the invention.

It may be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it may be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Patent Application Publication No. 2011/0177127: *Brucella abortus* Proteins and Methods of Use Thereof.

U.S. Pat. No. 7,541,447: Process for the Preparation of an Improved *Brucella* Strain Plasmid to Develop the Strain and the Vaccine Comprising the Said Strain.

1. Allen, C. A., L. G. Adams, and T. A. Ficht. 1998. Transposon-derived *Brucella abortus* rough mutants are attenuated and exhibit reduced intracellular survival. Infection and immunity 66:1008-1016.

2. Arenas-Gamboa, A. M., T. A. Ficht, M. M. Kahl-McDonagh, G. Gomez, and A. C. Rice-Ficht. 2009. The *Brucella abortus* S19 DeltavjbR live vaccine candidate is safer than S19 and confers protection against wild-type challenge in BALB/c mice when delivered in a sustained-release vehicle. Infection and immunity 77:877-884.

3. Ashford, D. A., J. di Pietra, J. Lingappa, C. Woods, H. Noll, B. Neville, R. Weyant, S. L. Bragg, R. A. Spiegel, J. Tappero, and B. A. Perkins. 2004. Adverse events in humans associated with accidental exposure to the livestock brucellosis vaccine RB51. Vaccine 22:3435-3439.

4. Bahlawane, C., B. Baumgarth, J. Serrania, S. Ruberg, and A. Becker. 2008. Fine-tuning of galactoglucan biosynthesis in Sinorhizobium meliloti by differential WggR (ExpG)-, PhoB-, and MucR-dependent regulation of two promoters. J Bacteriol 190:3456-3466.

5. Bahlawane, C., M. McIntosh, E. Krol, and A. Becker. 2008. Sinorhizobium meliloti regulator MucR couples exopolysaccharide synthesis and motility. Mol Plant Microbe Interact 21:1498-1509.

6. Bosseray, N., and M. Plommet. 1990. *Brucella suis* S2, *Brucella melitensis* Rev. 1 and *Brucella abortus* S19 living vaccines: residual virulence and immunity induced against three *Brucella* species challenge strains in mice. Vaccine 8:462-468.

7. Bossi, P., A. Tegnell, A. Baka, F. Van Loock, J. Hendriks, A. Werner, H. Maidhof, and G. Gouvras. 2004. Bichat guidelines for the clinical management of brucellosis and bioterrorism-related brucellosis. Euro Surveill 9:E15-16.

8. Cassataro, J., C. A. Velikovsky, S. de la Barrera, S. M. Estein, L. Bruno, R. Bowden, K. A. Pasquevich, C. A. Fossati, and G. H. Giambartolomei. 2005. A DNA vaccine coding for the *Brucella* outer membrane protein 31 confers protection against *B. melitensis* and *B. ovis* infection by eliciting a specific cytotoxic response. Infection and immunity 73:6537-6546.

9. Cassataro, J., C. A. Velikovsky, G. H. Giambartolomei, S. Estein, L. Bruno, A. Cloeckaert, R. A. Bowden, M. Spitz, and C. A. Fossati. 2002 Immunogenicity of the *Brucella melitensis* recombinant ribosome recycling factor-homologous protein and its cDNA. Vaccine 20:1660-1669.

10. Cespedes, S., E. Andrews, H. Folch, and A. Onate. 2000. Identification and partial characterisation of a new protective antigen of *Brucella abortus*. Journal of medical microbiology 49:165-170.

11. Costerton, J. W. 1995. Overview of microbial biofilms. Journal of industrial microbiology 15:137-140.

12. Costerton, J. W., Z. Lewandowski, D. E. Caldwell, D. R. Korber, and H. M. Lappin-Scott. 1995. Microbial biofilms. Annual review of microbiology 49:711-745.

13. Davos, D. E., C. F. Cargill, M. R. Kyrkou, J. A. Jamieson, and G. E. Rich. 1981. Outbreak of brucellosis at a South-Australian abattoir. 2. Epidemiological investigations. The Medical journal of Australia 2:657-660.

14. Delpino, M. V., S. M. Estein, C. A. Fossati, P. C. Baldi, and J. Cassataro. 2007. Vaccination with *Brucella* recombinant DnaK and SurA proteins induces protection against *Brucella abortus* infection in BALB/c mice. Vaccine 25:6721-6729.

15. Ficht, T. A., M. M. Kahl-McDonagh, A. M. Arenas-Gamboa, and A. C. Rice-Ficht. 2009. Brucellosis: the case for live, attenuated vaccines. Vaccine 27 Suppl 4:D40-43.

16. Ficht, T. A., J. Pei, and M. Kahl-McDonagh. 2010. In vitro mutagenesis of *Brucella* species. Methods in molecular biology (Clifton, N.J. 634:15-35.

17. Godefroid, M., M. V. Svensson, P. Cambier, S. Uzureau, A. Mirabella, X. De Bolle, P. Van Cutsem, G. Widmalm, and J. J. Letesson. *Brucella melitensis* 16M produces a mannan and other extracellular matrix components typical of a biofilm. FEMS Immunol Med Microbiol 59:364-377.

18. Guihot, A., P. Bossi, and F. Bricaire. 2004. [Bioterrorism with brucellosis]. Presse Med 33:119-122.

19. Hay, I. D., U. Remminghorst, and B. H. Rehm. 2009. MucR, a novel membrane-associated regulator of alginate biosynthesis in *Pseudomonas aeruginosa*. Applied and environmental microbiology 75:1110-1120.

20. Hong, P. 2005. Dissertation. Texas A&M University, College Station.

21. Hong, P. C., R. M. Tsolis, and T. A. Ficht. 2000. Identification of genes required for chronic persistence of *Brucella abortus* in mice. Infection and immunity 68:4102-4107.

22. Jamieson, J. A., G. E. Rich, M. R. Kyrkou, C. F. Cargill, and D. E. Davos. 1981. Outbreak of brucellosis at a South-Australian abattoir. 1. Clinical and serological findings. The Medical journal of Australia 2:593-596.

23. Kahl-McDonagh, M. M., A. M. Arenas-Gamboa, and T. A. Ficht. 2007. Aerosol infection of BALB/c mice with *Brucella melitensis* and *Brucella abortus* and protective efficacy against aerosol challenge. Infection and immunity 75:4923-4932.

24. Kahl-McDonagh, M. M., P. H. Elzer, S. D. Hagius, J. V. Walker, Q. L. Perry, C. M. Seabury, A. B. den Hartigh, R. M. Tsolis, L. G. Adams, D. S. Davis, and T. A. Ficht. 2006. Evaluation of novel *Brucella melitensis* unmarked deletion mutants for safety and efficacy in the goat model of brucellosis. Vaccine 24:5169-5177.

25. Kahl-McDonagh, M. M., and T. A. Ficht. 2006. Evaluation of protection afforded by *Brucella abortus* and *Brucella melitensis* unmarked deletion mutants exhibiting different rates of clearance in BALB/c mice. Infection and immunity 74:4048-4057.

26. Miller, C. D., J. R. Songer, and J. F. Sullivan. 1987. A twenty-five year review of laboratory-acquired human infections at the National Animal Disease Center. Am Ind Hyg Assoc J 48:271-275.

27. Montaraz, J. A., and A. J. Winter. 1986. Comparison of living and nonliving vaccines for *Brucella abortus* in BALB/c mice. Infection and immunity 53:245-251.

28. Mueller, K., and J. E. Gonzalez. Complex regulation of symbiotic functions is coordinated by MucR and quorum sensing in Sinorhizobium meliloti. J Bacteriol 193:485-496.

29. Nicoletti, P. 1990. Vaccination against *Brucella*. Advances in biotechnological processes 13:147-168.

30. Onate, A. A., S. Cespedes, A. Cabrera, R. Rivers, A. Gonzalez, C. Munoz, H. Folch, and E. Andrews. 2003. A DNA vaccine encoding Cu,Zn superoxide dismutase of *Brucella abortus* induces protective immunity in BALB/c mice. Infection and immunity 71:4857-4861.

31. Pappas, G., N. Akritidis, M. Bosilkovski, and E. Tsianos. 2005. Brucellosis. The New England journal of medicine 352:2325-2336.

32. Pasquevich, K. A., S. M. Estein, C. Garcia Samartino, A. Zwerdling, L. M. Coria, P. Barrionuevo, C. A. Fossati, G. H. Giambartolomei, and J. Cassataro. 2009. Immunization with recombinant *Brucella* species outer membrane protein Omp16 or Omp19 in adjuvant induces specific CD4+ and CD8+ T cells as well as systemic and oral protection against *Brucella abortus* infection. Infection and immunity 77:436-445.

33. Perkins, S. D., S. J. Smither, and H. S. Atkins. Towards a *Brucella* vaccine for humans. FEMS microbiology reviews.

34. Plommet, M., and N. Bosseray. 1977. [Checking of anti-*Brucella* vaccines by counting the *Brucella* in the spleen of intraperitoneally innoculated, vaccinated or unvaccinated, mice]. Journal of biological standardization 5:261-274.

35. Rinaudi, L. V., F. Sorroche, A. Zorreguieta, and W. Giordano. Analysis of the mucR gene regulating biosynthesis of exopolysaccharides: implications for biofilm formation in Sinorhizobium meliloti Rm1021. FEMS microbiology letters 302:15-21.

36. Saez, D., I. Guzman, E. Andrews, A. Cabrera, and A. Onate. 2008. Evaluation of *Brucella abortus* DNA and RNA vaccines expressing Cu—Zn superoxide dismutase (SOD) gene in cattle. Vet Microbiol 129:396-403.

37. Schurig, G. G., N. Sriranganathan, and M. J. Corbel. 2002. Brucellosis vaccines: past, present and future. Vet Microbiol 90:479-496.

38. Spink, W. W., J. W. Hall, 3rd, J. Finstad, and E. Mallet. 1962 Immunization with viable *Brucella* organisms. Results of a safety test in humans. Bull World Health Organ 26:409-419.

39. Winter, A. J., G. G. Schurig, S. M. Boyle, N. Sriranganathan, J. S. Bevins, F. M. Enright, P. H. Elzer, and J. D. Kopec. 1996. Protection of BALB/c mice against homologous and heterologous species of *Brucella* by rough strain vaccines derived from *Brucella melitensis* and *Brucella suis* biovar 4. American journal of veterinary research 57:677-683.

40. Wu, Q., J. Pei, C. Turse, and T. A. Ficht. 2006. Mariner mutagenesis of *Brucella melitensis* reveals genes with previously uncharacterized roles in virulence and survival. BMC Microbiol 6:102.

41. Kahl-McDonagh, M. M., and T. A. Ficht. 2006. Evaluation of protection afforded by *Brucella abortus* and *Brucella melitensis* unmarked deletion mutants exhibiting different rates of clearance in BALB/c mice. Infection & Immunity. 74(7):4048-57.

What is claimed is:

1. A vaccine composition for dogs comprising:
    a *Brucella canis* strain consisting of one or more attenuating gene knockouts selected from the group consisting of ΔvjbR and 16M ΔvjbR for attenuation in dogs; and
    a pharmaceutically acceptable vaccine carrier.

2. The vaccine composition of claim 1, wherein the composition further comprises an adjuvant.

3. The vaccine composition of claim 1, further comprising expressing one or more optional antibiotic resistance genes in the *Brucella canis* strain.

4. The vaccine composition of claim 1, wherein the vaccine is formulated for use in a prophylaxis, an amelioration of symptoms, a treatment, or any combinations thereof against brucellosis in a human or an animal subject.

5. The vaccine composition of claim 1, wherein the vaccine is formulated for administration via an oral, an intranasal, a parenteral, an intradermal, an intramuscular, an intraperitoneal, an intravenous, a subcutaneous, an epidural, a mucosal, a rectal, a vaginal, a sublingual, or a buccal route.

6. The vaccine composition of claim 1, further comprising an encapsulating agent that is an alginate bead or a microsphere.

* * * * *